United States Patent
Kim

(10) Patent No.: US 7,118,541 B2
(45) Date of Patent: Oct. 10, 2006

(54) LIE-DOWN MASSAGER

(76) Inventor: Hakjin Kim, 610 Ridgeview Ct., Diamond Bar, CA (US) 91785

( * ) Notice: Subject to any disclaimer, the term of this patent is extended or adjusted under 35 U.S.C. 154(b) by 303 days.

(21) Appl. No.: 10/249,915

(22) Filed: May 16, 2003

(65) Prior Publication Data

US 2004/0230145 A1 Nov. 18, 2004

(51) Int. Cl.
*A61H 7/00* (2006.01)
*A61H 15/00* (2006.01)

(52) U.S. Cl. .......... 601/15; 601/99; 601/100; 601/102; 601/116

(58) Field of Classification Search .......... 601/15, 601/18, 19, 86, 87, 90, 92–95, 97–103, 115, 601/116, 118, 122, 126; 606/240–242; 607/100; 5/617, 618
See application file for complete search history.

(56) References Cited

U.S. PATENT DOCUMENTS

| | | | |
|---|---|---|---|
| 2,193,882 A | 3/1940 | Petersen | |
| 2,310,106 A | 2/1943 | Miller | |
| 2,359,933 A | 10/1944 | Niblack | |
| 2,781,040 A | 2/1957 | Hill | |
| 2,874,689 A | 2/1959 | Gavelek | |
| 2,909,173 A | 10/1959 | Anderson | |
| 3,687,133 A | 8/1972 | Grubelic | |
| 3,877,422 A | 4/1975 | Heuser et al. | |
| 4,190,043 A | 2/1980 | Thompson | |
| 4,422,449 A | 12/1983 | Hamabe | |
| 4,458,675 A | 7/1984 | Nakao et al. | |
| 4,586,493 A | 5/1986 | Goodman | |
| 4,656,998 A | 4/1987 | Masuda et al. | |
| 4,899,403 A | 2/1990 | Yamasaki | |
| 4,947,833 A | 8/1990 | Yamasaki | |
| 5,038,757 A | 8/1991 | Yamasaki | |
| 5,088,475 A | 2/1992 | Steffensmeier | |
| 5,165,390 A | 11/1992 | Fleetwood | |
| 5,179,940 A | 1/1993 | Barreiro | |
| 5,755,677 A | 5/1998 | Masuda et al. | |
| 5,807,288 A | 9/1998 | Wu | |
| 5,971,944 A * | 10/1999 | Chang | 601/90 |
| 6,071,252 A | 6/2000 | Marcantoni | |
| 6,190,338 B1 | 2/2001 | Arndt | |
| 6,224,563 B1 | 5/2001 | Nonoue et al. | |
| 6,243,609 B1 | 6/2001 | Lee | |
| 6,409,689 B1 | 6/2002 | Chen | |
| 6,454,732 B1 | 9/2002 | Lee | |
| 6,542,779 B1 | 4/2003 | Lee | |
| 6,555,798 B1 | 4/2003 | Lee | |
| 6,591,141 B1 * | 7/2003 | Lee | 601/19 |
| 6,629,939 B1 | 10/2003 | Jikiba | |

(Continued)

*Primary Examiner*—Quang D. Thanh
(74) *Attorney, Agent, or Firm*—IPLA P.A.; James E. Bame

(57) ABSTRACT

A lie-down massager comprises a frame, a rider below a top panel of the frame, a guide member engaged between the frame and the rider to allow a horizontal reciprocation to the rider, and a lifter carrying massage bumps. A gear unit includes a bolt gear downwardly extending from the lifter, a nut type gear having a outer periphery, a first gear incorporated on the periphery, and a second gear engaged to the first gear. The bolt gear is releasably engaged in the nut type gear whose bottom end is rotatably attached to and supported by the rider, whereby the second gear rotation generates the first gear rotation and the subsequent rotation of the nut type gear enables the lifter to make a vertical reciprocation by the releasable engagement of the bolt gear and the nut type gear.

19 Claims, 5 Drawing Sheets

U.S. PATENT DOCUMENTS 6,643,551 B1    11/2003  Park
6,849,054 B1 *   2/2005  Kim .......................... 601/98
6,890,313 B1 *   5/2005  Kim .......................... 601/99
2002/0138023 A1   9/2002  Kume et al.
2002/0193713 A1  12/2002  Lee
2003/0018284 A1   1/2003  Lim

* cited by examiner

LIE-DOWN MASSAGER

BACKGROUND OF INVENTION

The invention relates generally to a massaging device. More particularly, the present invention relates to an improved lie-down massager capable of efficiently treating bodily malfunctions such as back pain and gastrointestinal weakness by applying a therapeutic massaging treatment along the back and neck of a patient lying down on the massager whose massaging bumps move horizontally and vertically along the patients spinal cord and neck in which the vertical movement of the massaging bumps are actuated by adopting a bolt gear and an elongated nut type gear to work in a combination gear mechanism.

Conventional bed or mat type massaging devices employ a spring mechanism for vertically moving massaging bumps. As disclosed U.S. Pat. No. 6,454,732, a spring mechanism allows the massaging bumps to gently move up and down. However, when it comes to therapeutic effects, the spring mechanism proves too soft to push up the massaging bumps when stronger pressure is required, because tension of springs applies equally to patients lying on the massaging device regardless of patients requirements.

A demand is to adopt a reliable mechanism demonstrating a steady and robust therapeutic effects while stabilizing the vertical movement of the massaging bumps.

SUMMARY OF INVENTION

The present invention is contrived to overcome the conventional disadvantages. Accordingly, an object of the invention is to provide a lie-down massager that improves therapeutic effects by adopting a combination gear mechanism for a vertical movement of massaging bumps.

Another object is to stabilize the vertical movement of the massaging bumps, thereby enabling patients to receive a steady and robust massaging therapy with the massaging bumps applied to and along their backs and necks. A further object is to improve product reliability and customer satisfaction by mechanically stabilizing the vertical movement of the massaging bumps in accordance with adopting the combination gear mechanism employing a bolt gear and an elongated nut type gear.

To achieve these and other objects, the lie-down massager according to the present invention comprises a base frame having an elongated top panel with an elongated opening formed centrally and lengthwisely through the elongated top panel. A rider is provided below the elongated top panel of the base frame, and a guide member is movably engaged between the base frame and the rider so as to enable the rider to make a horizontally reciprocal movement relative to the base frame. There is also provided a lifter having a top portion and a bottom portion where elongated guides extend marginally from the bottom portion of the lifter and are releasably received by guide bushes formed on top of the rider to stabilize a vertically reciprocal movement of the lifter relative to the rider.

In a preferred embodiment, a gear unit is provided to include a bolt gear downwardly extending from the bottom portion of the lifter, an elongated nut type gear having a circular outer periphery, a first gear incorporated on and along the circular outer periphery, and a second gear engaged to the first gear and connected to a first motor attached to the rider. Here, the bolt gear is releasably engaged in the nut type gear whose bottom end is rotatably attached to and supported by the rider, whereby the second gear rotation generates the first gear rotation and the subsequent rotation of the nut type gear enables the lifter to make a vertically reciprocal movement in accordance with the releasable engagement of the bolt gear and the nut type gear.

To enhance therapeutic massaging effect, massage bumps are attached to the top portion of the lifter and moving vertically and/or horizontally along the elongated opening of the elongated top panel of the base frame, and a pad covering the massage bumps and the elongated opening of the base frame.

Alternately, either a pair of side rack gears or pulleys are provided to facilitate the horizontal reciprocation of the rider. The side rack gears may be parallel to each other and lengthwisely provided in the base frame with a roller gear perpendicular to the side rack gears and rollably connected to the rider and rotatably mounted on the side rack gears. Meanwhile, the pulleys may be linked by a rope and respectively mounted in a front end portion and a rear end portion of the base frame, wherein a predetermined portion of the rope is fixedly attached to the rider so that the pulley rotation enables the rider to generate a horizontally reciprocal movement along the elongated top opening.

A pair of roller coasters are provided parallel to each other and attached to the base frame so as to each have a substantially waved top surface. In this construction, a coasting member liftedly engaged on top of the rider with a coaster guide roller formed outwardly extending from each side surface of the coasting member. The coaster guide roller enables the coasting member to make a roller coasting movement on and along the waved top surfaces of the roller coasters.

It is preferred that the first and second gears are formed of bevel gears. Selectively, the second gear may be a spirally threadedshaft and the first gear is radially embayed. The lie-down massager of claim 1 wherein the massage bumps are roller balls partitioned to first and second pairs, wherein the first pair bumps are aligned parallel to the second pair bumps. The massager further comprises first and second bump holders propping and maintaining the first and second pair bumps above the top portion of the lifter, wherein the first and second bump holders are tapered toward each lower end thereof, a first engagement member to rockingly engage the lower ends of the bump holders to the top portion of the lifter, and a second engagement member to rollingly engage the massage bumps thereto. The massage bumps each include a heater in form of a heating lamp generating heat and infrared rays.

Advantages of the present inventions are numerous. Most of all, the combination gear mechanism employing a bolt gear and an elongated nut type gear for the vertical movement of the massaging bumps substantially alleviates pains resulting from the conventional massager using a predetermined solid pattern along which the rider follows without a vertically allowed resilience, thereby improving product reliability and customer satisfaction. Also, the combination gear mechanism minimizes parts required for the vertical reciprocation of the massaging bumps while improving stability and controllability of the vertical reciprocation of the lifter carrying the massaging bumps. In addition, the coasting member working with the roller coasters to realize an additional lifting by utilizing the horizontally reciprocal movement of the rider enables the massaging bumps to continue a smooth, steady and robust massaging on the patient, thereby substantially improving massaging effect and subsequently maximizing customer satisfaction.

Although the present invention is briefly summarized, the full understanding of the invention can be obtained by the following drawings, detailed description and appended claims.

BRIEF DESCRIPTION OF DRAWINGS

These and other features, aspects and advantages of the present invention will become better understood with reference to the accompanying drawings, wherein.

DETAILED DESCRIPTION

Figure 1:
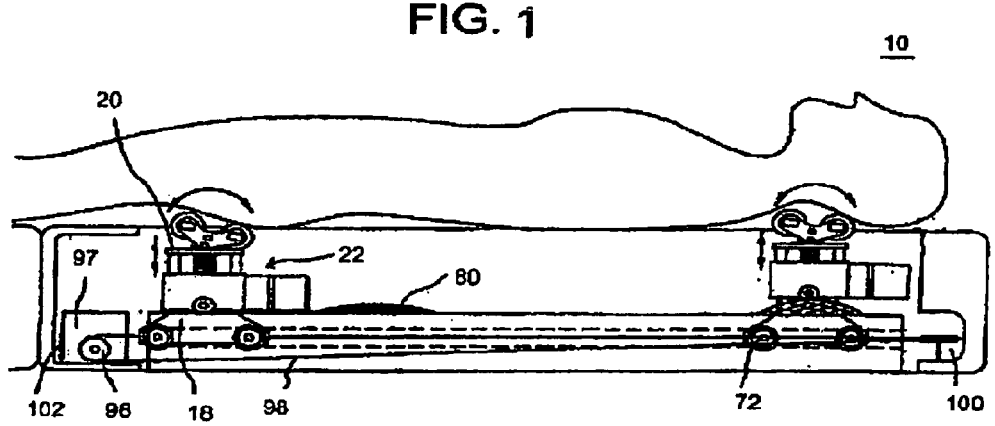
FIG. 1 is a view showing a lie-down massager with a patient lying thereon according to the present invention.
Figure 2:
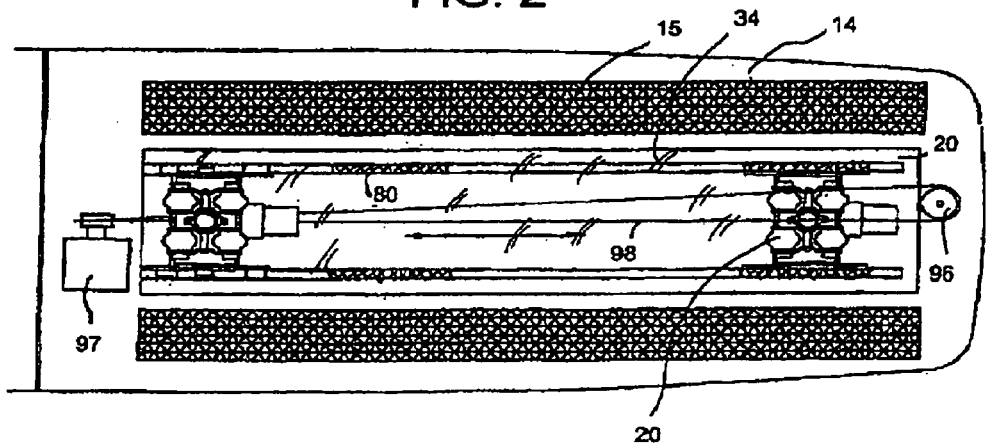
FIG. 2 is a plan view showing the lie-down massager without the patient in FIG. 1.

FIG. 1 shows a brief massaging mechanism of a lie-down massager 10 according to the present invention with a patient lying thereon for a bodily massage, and FIG. 2 shows a plan view of the massager 10 excluding the patient. As shown therein, the lie-down massager 10 includes a base frame 12 in a bed type or a mat type. The base frame 12 includes an elongated top panel 14 with a heating member 15 spread in the top panel 14 to further comfort the patient on the massager 10. An elongated opening 16 is formed centrally and lengthwisely through the elongated top panel 14. The heating member 15 is preferably formed around the elongated opening 16 to generate heat rays at a predetermined temperature. The massager 10 includes a rider 18 and a lifter 20. The rider 18 is provided below the elongated top panel 14 of the base frame 12. A guide member 22 is movably engaged between the base frame 12 and the rider 18 so as to enable the rider 18 to make a horizontally reciprocal movement relative to the base frame 12. Here, the guide member 22 may be formed of either a rope-pulley mechanism or a rack gear mechanism.

Figure 3:
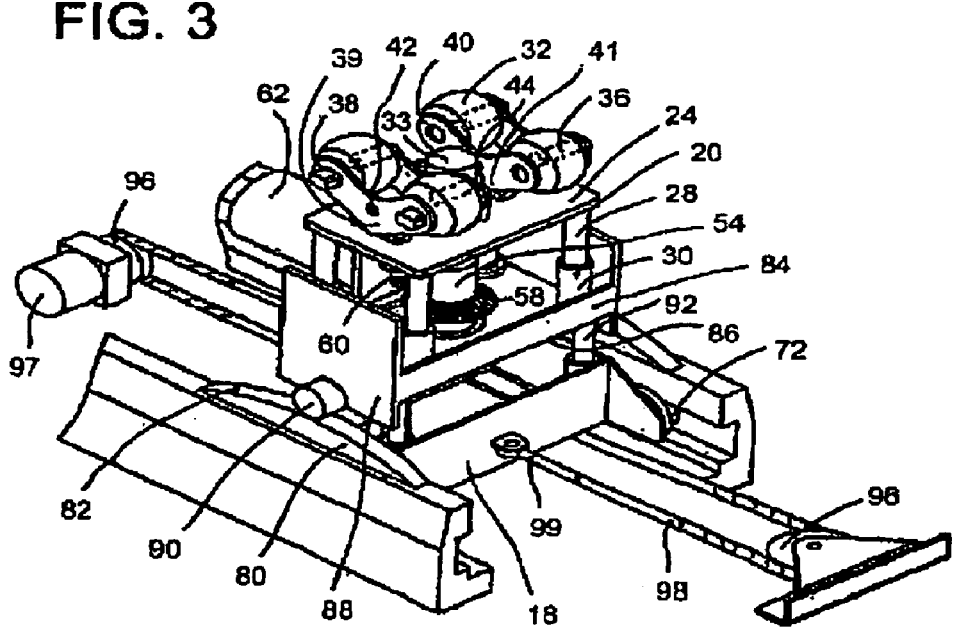
FIG. 3 is a perspective view showing an overall mechanism of the lie-down massager according to the present invention.
Figure 4:
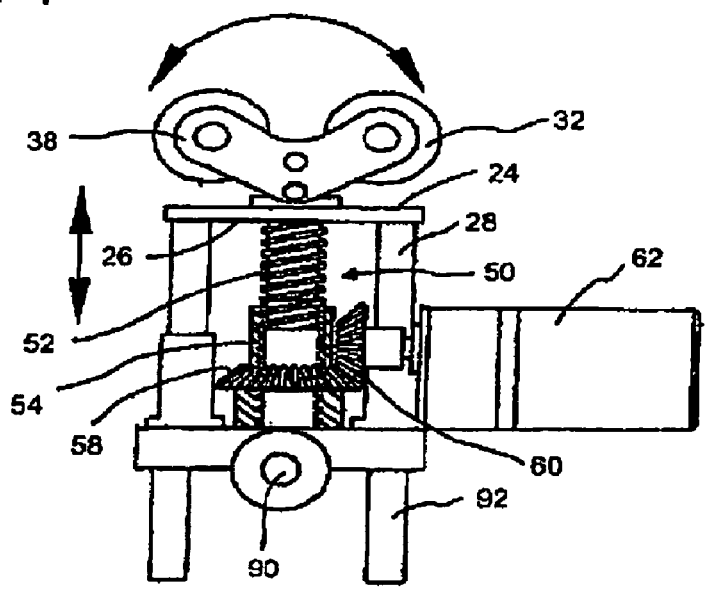
FIG. 4 is a construction view showing a combination gear mechanism in FIG. 3.

As shown in FIGS. 3 and 4 further illustrating the massaging mechanism, the lifter 20 has a top portion 24 and a bottom portion 26. In this construction, elongated guides 28 extend marginally from the bottom portion 26 of the lifter 20. The elongated guides 28 are releasably received by guide bushes 30 formed on top of the rider 18 so as to stabilize a vertically reciprocal movement of the lifter 20 relative to the rider 18. In a better version, the elongated guides 28 are formed in pins and the guide bushes 30 are formed in pin-receiving bushes.

In order to implement a therapeutic massage operation, a plurality of massage bumps 32 are attached to the top portion 24 of the lifter 20. The massage bumps 32 are provided to move vertically and/or horizontally along the elongated opening 16 of the elongated top panel 14 of the base frame 12. So the massage bumps 32 are directed to massage the back and neck of the patient lying on the top panel 14 of the base frame 12. Here, a pad 34 may be provided to cover the massage bumps 32 and the elongated opening 16 of the base frame 12.

The massage bumps 32 are preferably partitioned to first and second pairs so that the first pair bumps are aligned parallel to the second pair bumps. It is also recommended that the massage bumps 32 are formed of roller balls which are preferably formed of precious stone such as jade or gem. For a better massaging result, the massage bumps 32 may each include a heater 36 preferably in form of a heating lamp. Selectively, the heating lamp for the heater 36 may be formed to generate heat and infrared rays to maximize therapeutic effects. In a preferred mode, first and second bump holders 38, 40 are provided to prop and maintain the first and second pair bumps above the top portion 24 of the lifter 20. The first and second bump holders 38, 40 are preferably tapered toward each lower end 39, 41 thereof. To improve flexibility of engagement between the bump holders 38, 40 and the bumps 32, and between the bump holders 38, 40 and the lifter 20, there are provided first and second engagement members 42, 44. The first engagement member 42 is provided to rockingly engage the lower ends 39, 41 of the bump holders 38, 40 to the top portion 24 of the lifter 20. The second engagement member 44 is provided to rollingly engage the massage bumps 32 to itself.

The engagement members 42, 44 each may be a bolt, a roller, or other engagement tool. In this bump-holder mechanism, the bump holders 38, 40 flexibly engage the massage bumps 32 to the top portion 24 of the lifter 20 so that the massage bumps 32 rollingly massage the back and neck of the patient lying on the base frame 12 while evenly spreading the massaging power along the bodily portions being pushed up by the massage bumps 32. That is, the rocking mechanism of the bump holders 38, 40 enables the massage bumps 32 to smoothly follow the curvature of a spinal cord of the patient lying on the base frame 12 while each of the massage bumps 32 evenly delivers the massaging power to the patients bodily portions being massaged. Selectively, a center bump 33 may be provided between the massage bumps 32 and on the top surface 24 of the lifter 20 for a solid massage function relative to the rocking massage of the massage bumps 32.

Figure 5:
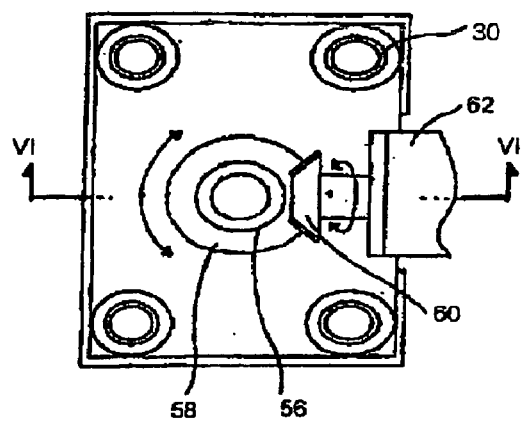
FIG. 5 is a schematic plan view showing the combination gear mechanism according to a first embodiment of the present invention.
Figure 6A:
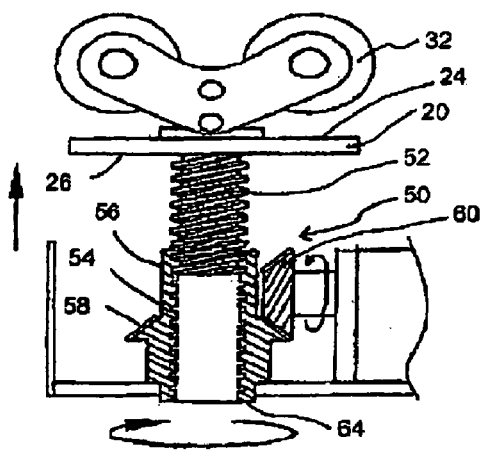
FIGS. 6A and 6B are operational views applied from a cross-section taken along VI—VI in FIG. 5.
Figure 6B:
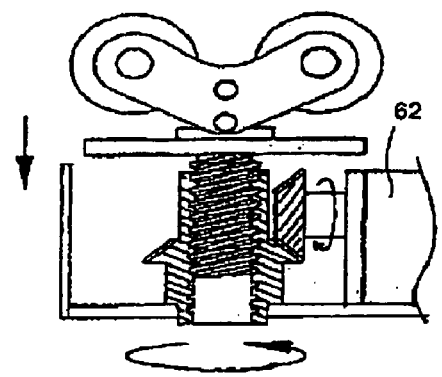

FIGS. 5 and 6A–6B each illustrate a bevel gear application for the bump lifting mechanism. As shown therein, in order to realize a stabilized lifting mechanism of the lifter 20 relative the rider 18 or the guide member 22, a gear unit 50 is provided to include a bolt gear 52 downwardly extending from the bottom portion 26 of the lifter 20. To match with the bolt gear 52, an elongated nut type gear 54 includes a circular outer periphery 56, a first gear 58 incorporated on and along the circular outer periphery 56, and a second gear 60 engaged to the first gear 58 and connected to a first motor 62 attached to the rider 18 or the guide member 22. It is preferred that the first and second gears 58, 60 are bevel gears engaged to each other in a perpendicular format so that the first gear 58 becomes perpendicular to the second gear 60. In this construction, the bolt gear 52 is releasably engaged in the nut type gear 54 whose bottom end 64 is rotatably attached to and supported by the rider 18 or the guide member 22, whereby the second gear rotation generates the first gear rotation and the subsequent rotation of the nut type gear 54 enables the lifter 20 to make a vertically reciprocal movement in accordance with the releasable engagement of the bolt gear 52 and the nut type gear 54.

Figure 7:
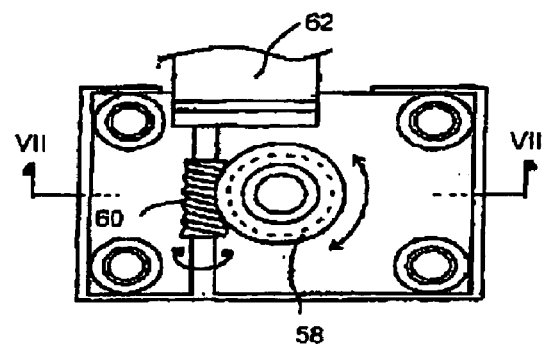
FIG. 7 is a schematic plan view showing the combination gear mechanism according to a second embodiment of the present invention.
Figure 8A:
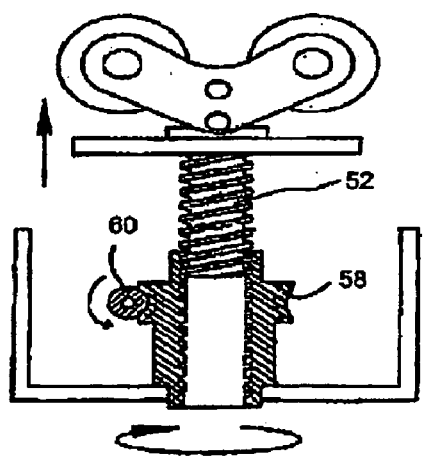
FIGS. 8A and 8B are operational views applied from a cross-section taken along VIII—VIII in FIG. 5.
Figure 8B:
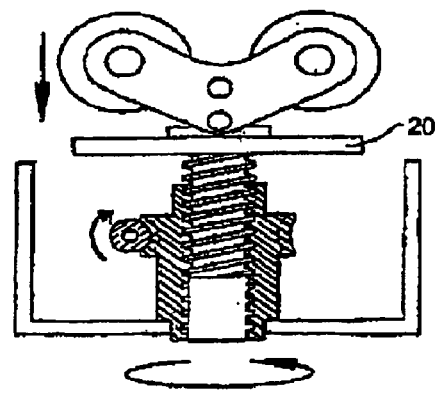

Alternately, as shown in FIGS. 7 and 8A–8B each illustrating a worm gear application for the bump lifting mechanism, the first gear. 58 may be formed in a radial embayment format and the second gear 60 may be formed in a spirally threaded shaft format so as to stabilize the bump lifting mechanism. That is, the second gear 60 is formed in a worm gear and the first gear 58 is formed in a wheel gear with its marginal teeth operatively meshed into those of the second gear 60. The combination gear mechanism either in the worm gear application or in the bevel gear application serves to improve efficiency of the lifter-lifting operation.

Figure 9:
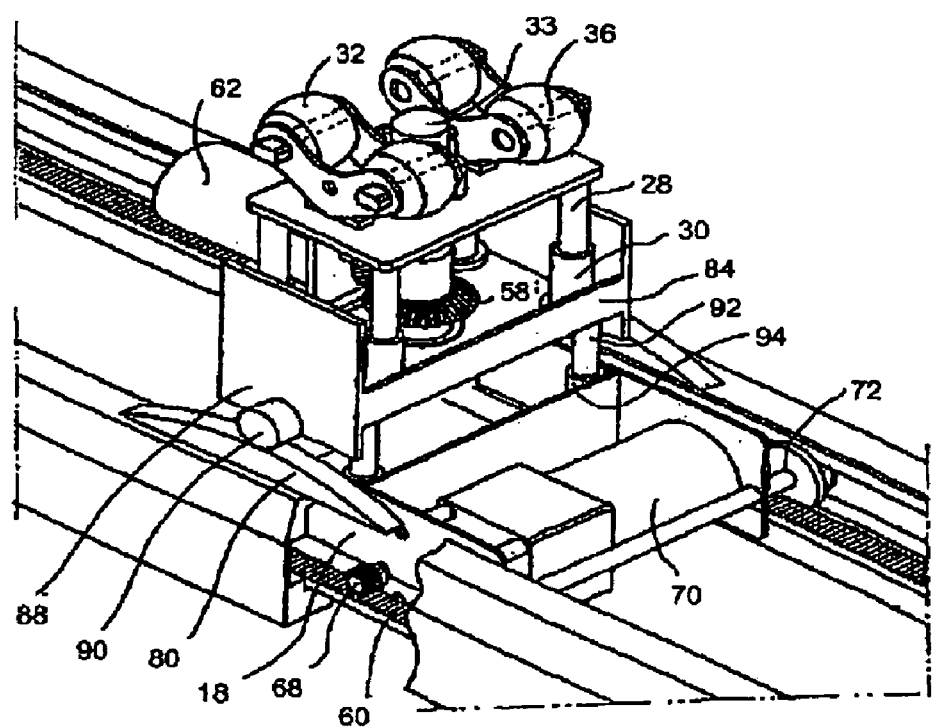
FIG. 9 is a perspective view showing a rack gear application according to the present invention.

Meanwhile, as shown in FIG. 9, when the guide member 22 is incorporated in the rack gear mechanism, the guide member 22 comprises a pair of side rack gears 66 parallel to each other and lengthwisely provided below the elongated top panel 14 of the base frame 12, a roller gear 68 perpendicular to the side rack gears 66, and a second motor 70 to power the roller gear 68. Here, the roller gear 68 is rollably connected to the rider 18 and rotatably mounted on the side rack gears 66. In this construction, the roller gear 68 is rotatably mounted on the rack gears 66 to allow the rider 18 to make the horizontal reciprocation along the rack gears 66 where the rider 18 is also maintained below the elongated top panel 14 of the base frame 12. Here, a plurality of guider rollers 72 may be formed from each side of the rider 18 to further stabilize the horizontally reciprocal movement of the rider 18 along the rack gears 66. The roller gear 68 is powered by the second motor 70 fixed to the rider 18.

As further shown in FIG. 9, a pair of roller coasters 80 parallel to each other and to the rack gears 66 are attached to the base frame 12 to allow the horizontally moving rider 18 to pass therebetween. The roller coasters 80 are each formed to have a substantially waved top surface 82. In this construction, a coasting member 84 having a bottom surface 86 and side surfaces 88 is liftedly engaged to the rider 18. A guide roller 90 is formed outwardly extending from the side surfaces 88 of the coasting member 84. Here, the guide roller 90 on each of the side surfaces 88 enables the coasting member 84 to make a roller coasting movement on and along the waved top surfaces 82 of the roller coasters 80 while being engagedly lifted from the rider 18 which makes the horizontally reciprocal movement. Preferably, the coasting member 84 is formed in a container type.

So the first elongated guides 28 come to be releasably received by the first guide bushes 30 marginally formed on top of the coasting member 84 in order to stabilize the vertically reciprocal movement of the lifter 20 relative to the coasting member 84. In the better version, the waved top surfaces 82 of the roller coasters 80 each substantially form a curvature of a human spinal cord. Meanwhile, second elongated guides 92 are provided extending from the bottom surface 86 of the coasting member 84, and second guide bushes 94 are upwardly formed on the rider 18 to releasably receive the second elongated guides 92 so as to stabilize the roller coasting movement of the coasting member 84 along the roller coasters 80 and the lifting of the coasting member 84 from the rider 18.

As shown back in FIG. 3, the guide member 22 may be incorporated in a pair of pulleys 96 linked by a rope 98 and respectively mounted in a front end portion 100 and a rear end portion 102 of the base frame 12. A predetermined portion 99 of the rope 98 is fixedly attached to the rider 18 so that the pulley rotation enables the rider 18 to generate a horizontally reciprocal movement along the elongated top opening 16. There is also provided a pulley motor 97 that controls one of the pulleys 96. In a preferred version, the pulley motor 97 is provided adjacent to the pulley 96 provided in the rear end portion 102 of the base frame 12. Preferably, the pulleys 96 are relatively twisted by 90 degrees against each other to facilitate the horizontal reciprocation of the rider 18.

As discussed above, an advantage of the present invention is that the combination gear mechanism employing the bolt gear 52 and the elongated nut type gear 54 for the vertical movement of the massaging bumps 32 substantially alleviates pains resulting from the conventional massager using a predetermined solid pattern along which the rider 18 follows without a vertically allowable resilience, thereby improving product reliability. Further, the combination gear mechanism minimizes parts required for the vertical reciprocation of the massaging bumps 32 while improving stability and controllability of the vertical reciprocation of the lifter 20 carrying the massaging bumps 32. In addition, the coasting member 84 working with the roller coasters 80 to realize an additional lifting by utilizing the horizontally reciprocal movement of the rider 18 enables the massaging bumps 32 to continue a smooth, steady and robust massaging on the patient, thereby substantially improving massaging effect and subsequently maximizing customer satisfaction.

Although the invention has been described in considerable detail, other versions are possible by converting the aforementioned construction. Therefore, the scope of the invention shall not be limited by the specification specified above and the appended claims.

The invention claimed is:

1. A lie-down massager, comprising:
a) a base frame having an elongated top panel, wherein an elongated top opening is formed centrally and lengthwisely through the elongated top panel;
b) a rider provided below the elongated top panel;
c) a pair of pulleys linked by a rope and respectively mounted in a front end portion and a rear end portion of the base frame, wherein a predetermined portion of the rope is fixedly attached to the rider so that the pulley rotation enables the rider to generate a horizontally reciprocal movement along the elongated top opening;
d) a pair of roller coasters parallel to each other and attached to the base frame, wherein the roller coasters each have a substantially waved top surface;
e) a coasting member liftedly engaged on top of the rider, wherein a coaster guide roller is formed outwardly extending from each side surface of the coasting member, wherein the coaster guide roller enables the coasting member to make a roller coasting movement on and along the waved top surfaces of the roller coasters;
f) a lifter having a top portion and a bottom portion, wherein first elongated guides extend marginally from the bottom portion of the lifter, wherein the elongated guides are releasably received by first guide bushes formed on top of the coasting member to stabilize a vertically reciprocal movement of the lifter relative to the rider, wherein second elongated guides downwardly extending from the coasting member, and wherein second guide bushes upwardly formed on the rider to releasably receive the second elongated guides so as to stabilize the roller coasting movement of the coasting member along the roller coasters and the lifting of the coasting member from the rider;
g) a gear unit including a bolt gear downwardly extending from the bottom portion of the lifter, an elongated nut type gear having a circular outer periphery, a first gear incorporated on and along the circular outer periphery, and a second gear engaged to the first gear and connected to a motor attached to the coasting member, wherein the bolt gear is releasably engaged in the nut type gear whose bottom end is rotatably attached to and supported by the coasting member, whereby the second gear rotation generates the first gear rotation and the subsequent rotation of the nut type gear enables the lifter to make a vertically reciprocal movement in accordance with the releasable engagement of the bolt gear and the nut type gear;

h) massage bumps attached to the top portion of the lifter and moving vertically and/or horizontally along the elongated top opening of the elongated top panel of the base frame; and i) a pad covering the massage bumps and the elongated top opening of the base frame.

2. The lie-down massager of claim 1 wherein the first and second gears are bevel gears.

3. The lie-down massager of claim 1 wherein the second gear is a spirally threadedshaft.

4. The lie-down massager of claim 1 wherein the second gear is a spirally threaded shaft and the first gear is radially embayed.

5. The lie-down massager of claim 1 further comprises rider guide rollers on each side of the rider, wherein the rider guide rollers are rollably engaged in the base frame to guide the horizontally reciprocal movement of the rider.

6. The lie-down massager of claim 1 wherein the massage bumps are roller balls partitioned to first and second pairs, wherein the first pair bumps are aligned parallel to the second pair bumps.

7. The lie-down massager of claim 6 further comprising:

a) first and second bump holders propping and maintaining the first and second pair bumps above the top portion of the lifter, wherein the first and second bump holders are tapered toward each lower end thereof;

b) a first engagement member to rockingly engage the lower ends of the bump holders to the top portion of the lifter; and c) second engagement member to rollingly engage the massage bumps thereto.

8. The lie-down massager of claim 1 wherein the massage bumps each include a heater, wherein the heater is a heating lamp generating heat and infrared rays.

9. The lie-down massager of claim 1 wherein the waved top surfaces of the roller coasters each substantially form a curvature of a human spinal cord.

10. The lie-down massager of claim 1 further comprising a heating member spread in the top panel of the base frame.

11. A lie-down massager, comprising:

a) a base frame having an elongated top panel, wherein an elongated opening is formed centrally and lengthwisely through the elongated top panel;

b) a pair of rack gears parallel to each other and provided below the elongated top panel;

c) a rider having a roller gear perpendicular to the rack gears, wherein the roller gear is rotatably mounted on the rack gears to allow the rider to make a horizontally reciprocal movement along the rack gears, wherein the rider is maintained below the elongated top panel;

d) a pair of roller coasters parallel to each other and attached to the base frame, wherein the roller coasters each have a substantially waved top surface;

e) a coasting member liftedly engaged on top of the rider, wherein a coaster guide roller is formed outwardly extending from each side surface of the coasting member, wherein the coaster guide roller enables the coasting member to make a roller coasting movement on and along the waved top surfaces of the roller coasters;

f) a lifter having a top portion and a bottom portion, wherein first elongated guides extend marginally from the bottom portion of the lifter, wherein the elongated guides are releasably received by first guide bushes formed on top of the coasting member to stabilize a vertically reciprocal movement of the lifter relative to the rider, wherein second elongated guides downwardly extending from the coasting member; and second guide bushes upwardly formed on the rider to releasably receive the second elongated guides so as to stabilize the roller coasting movement of the coasting member along the roller coasters and the lifting of the coasting member from the rider;

g) a gear unit including a bolt gear downwardly extending from the bottom portion of the lifter, an elongated nut type gear having a circular outer periphery, a first gear incorporated on and along the circular outer periphery, and a second gear engaged to the first gear and connected to a motor attached to the coasting member, wherein the bolt gear is releasably engaged in the nut type gear whose bottom end is rotatably attached to and supported by the coasting member, whereby the second gear rotation generates the first gear rotation and the subsequent rotation of the nut type gear enables the lifter to make a vertically reciprocal movement in accordance with the releasable engagement of the bolt gear and the nut type gear;

h) massage bumps attached to the top portion of the lifter and moving vertically and/or horizontally along the elongated top opening of the elongated top panel of the base frame; and i) a pad covering the massage bumps and the elongated top opening of the base frame.

12. The lie-down massager of claim 11 wherein the first and second gears are bevel gears.

13. The lie-down massager of claim 11 wherein the second gear is a spirally threadedshaft, and the first gear is radially embayed.

14. The lie-down massager of claim 11 further comprises rider guide rollers on each side of the rider, wherein the rider guide rollers are rollably engaged in the base frame to guide the horizontally reciprocal movement of the rider.

15. The lie-down massager of claim 11 wherein the massage bumps are roller balls partitioned to first and second pairs, wherein the first pair bumps are aligned parallel to the second pair bumps.

16. The lie-down massager of claim 15 further comprising:

a) first and second bump holders propping and maintaining the first and second pair bumps above the top portion of the lifter, wherein the first and second bump holders are tapered toward each lower end thereof;

b) a first engagement member to rockingly engage the lower ends of the bump holders to the top portion of the lifter; and c) a second engagement member to rollingly engage the massage bumps thereto.

17. The lie-down massager of claim 11 wherein the massage bumps each include a heater, wherein the heater is a heating lamp generating heat and infrared rays.

18. The lie-down massager of claim 11 wherein the waved top surfaces of the roller coasters each substantially form a curvature of a human spinal cord.

19. The lie-down massager of claim 11 further comprising a heating member spread in the top panel of the base frame.

* * * * *